United States Patent
Namiki

(10) Patent No.: US 9,974,620 B2
(45) Date of Patent: May 22, 2018

(54) MANIPULATOR SYSTEM, AND MEDICAL SYSTEM

(71) Applicant: OLYMPUS CORPORATION, Tokyo (JP)

(72) Inventor: Hirotaka Namiki, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days. days.

(21) Appl. No.: 15/590,289

(22) Filed: May 9, 2017

(65) Prior Publication Data

US 2017/0239008 A1    Aug. 24, 2017

Related U.S. Application Data

(63) Continuation of application No. PCT/JP2016/051894, filed on Jan. 22, 2016.

(30) Foreign Application Priority Data

Feb. 25, 2015  (JP) .................................. 2015-034815

(51) Int. Cl.
| | |
|---|---|
| *A61B 17/00* | (2006.01) |
| *A61B 34/35* | (2016.01) |
| *A61B 34/20* | (2016.01) |
| *A61B 34/00* | (2016.01) |
| *A61B 34/30* | (2016.01) |
| *A61B 34/37* | (2016.01) |

(52) U.S. Cl.
CPC ............. *A61B 34/35* (2016.02); *A61B 34/20* (2016.02); *A61B 34/70* (2016.02); *A61B 34/30* (2016.02); *A61B 34/37* (2016.02); *A61B 2034/2048* (2016.02); *A61B 2034/2065* (2016.02); *A61B 2034/301* (2016.02); *A61B 2034/742* (2016.02)

(58) Field of Classification Search
CPC ......... A61B 34/35; A61B 34/20; A61B 34/70; A61B 34/30; A61B 34/37; A61B 2090/701
USPC ........... 700/261; 600/104, 117, 118; 604/264
See application file for complete search history.

(56) References Cited

U.S. PATENT DOCUMENTS

| | | |
|---|---|---|
| 8,682,489 B2 | 3/2014 | Itkowitz et al. |
| 2008/0234866 A1 | 9/2008 | Kishi et al. |
| 2010/0134327 A1* | 6/2010 | Dinh ...................... G06F 3/014 |
| | | 341/20 |

(Continued)

FOREIGN PATENT DOCUMENTS

| | | |
|---|---|---|
| JP | H05-261691 A | 10/1993 |
| JP | 2008-228967 A | 10/2008 |

(Continued)

OTHER PUBLICATIONS

International Search Report dated Mar. 15, 2016 issued in PCT/JP2016/051894.

*Primary Examiner* — Dalena Tran
(74) *Attorney, Agent, or Firm* — Scully, Scott, Murphy & Presser, P.C.

(57) ABSTRACT

A manipulator system 1 includes an arm that is operated such that a manipulator 3 is put into actuation, a tapping sensor unit 22 that is provided on the arm and detects tapping by an operator on the arm, a system control unit 4 that implements control set for each tapping in association with tapping detected by the tapping sensor unit 22.

8 Claims, 10 Drawing Sheets

(56) References Cited

U.S. PATENT DOCUMENTS

| | | | | |
|---|---|---|---|---|
| 2011/0118748 A1* | 5/2011 | Itkowitz | ............. | A61B 19/2203 |
| | | | | 606/130 |
| 2011/0118752 A1 | 5/2011 | Itkowitz et al. | | |
| 2012/0184955 A1* | 7/2012 | Pivotto | ............. | A61B 19/2203 |
| | | | | 606/41 |
| 2014/0267024 A1* | 9/2014 | Keller | .................... | G06F 3/017 |
| | | | | 345/156 |

FOREIGN PATENT DOCUMENTS

| | | |
|---|---|---|
| JP | 2009-262291 A | 11/2009 |
| JP | 2013-510672 A | 3/2013 |
| JP | 2014-184494 A | 10/2014 |

* cited by examiner

MANIPULATOR SYSTEM, AND MEDICAL SYSTEM

CROSS-REFERENCE TO RELATED APPLICATIONS

This application is a continuation claiming priority on the basis of Japan Patent Application No. 2015-034815 applied in Japan on Feb. 25, 2015 and based on PCT/JP2016/051894 filed on Jan. 22, 2016. The contents of both the PCT application and the Japan Application are incorporated herein by reference.

BACKGROUND OF THE INVENTION AND RELATED ART STATEMENT

The present invention relates to a manipulator system, and a medical system that is inserted through the body cavity of a patient for surgical operations to view, and apply treatments or the like to, the patient's body cavity.

Medical equipments including a treatment tool to be inserted through the body cavity of a patient have widely been used to pull the distal end of the treatment tool as by means of a wire for the purpose of viewing, and applying treatments to, organs in the body cavity. In recent years, the structure of such medical equipments has become more complicated and sophisticated because of the need for being compatible with some diverse treatments. Structural complication and sophistication have led to more complicated and sophisticated operations or manipulations accordingly.

JP(A) 2009-262291 discloses a manipulator system that relies upon a joystick type manipulator, an arm type manipulator, a touchpad type manipulator, and a footswitch to improve on manipulation capabilities.

SUMMARY OF INVENTION

According to one embodiment. A manipulator system includes:
an arm that is operated such that a manipulator is put into actuation;
a tapping sensor unit that is provided on the arm and detects tapping by an operator on the arm;
a system control unit that implements control set for each tapping in association with tapping detected by the tapping sensor unit.

DESCRIPTION OF EMBODIMENTS

Some embodiments will now be explained.

Figure 1:
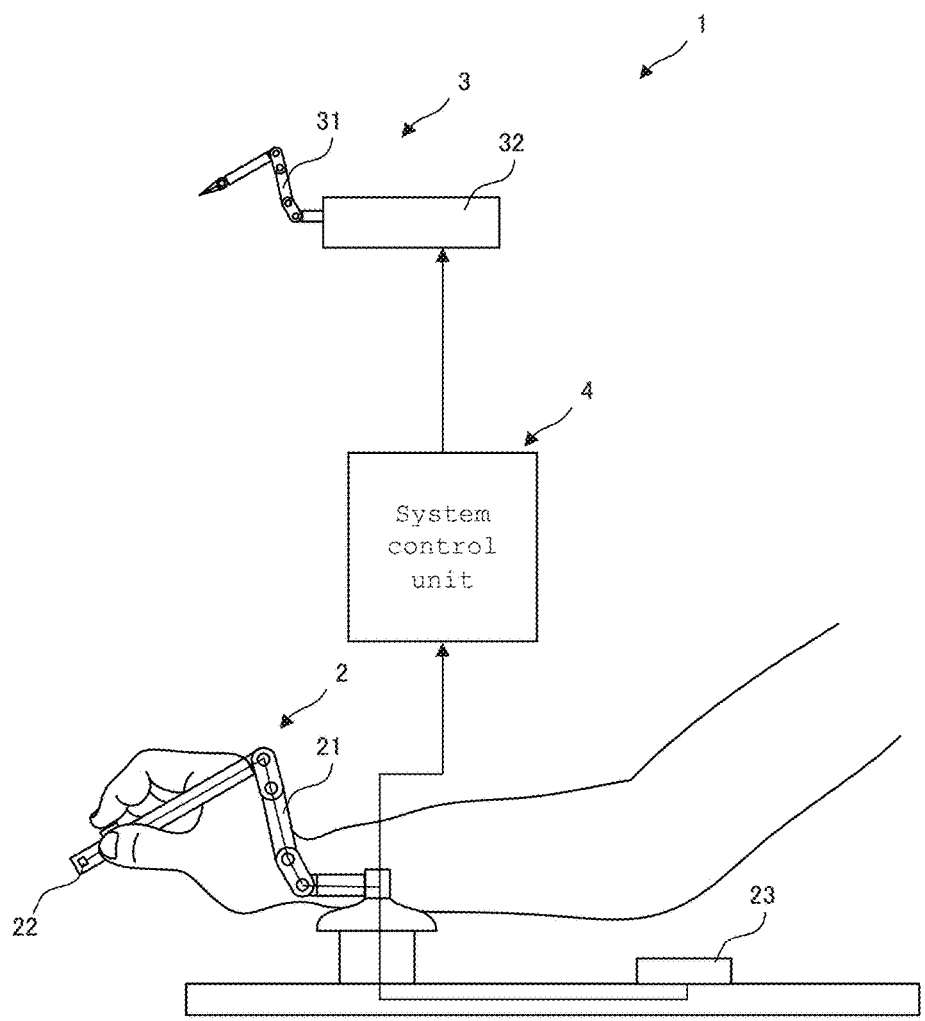
FIG. 1 shows the manipulator system according to one embodiment described herein.
Figure 2:
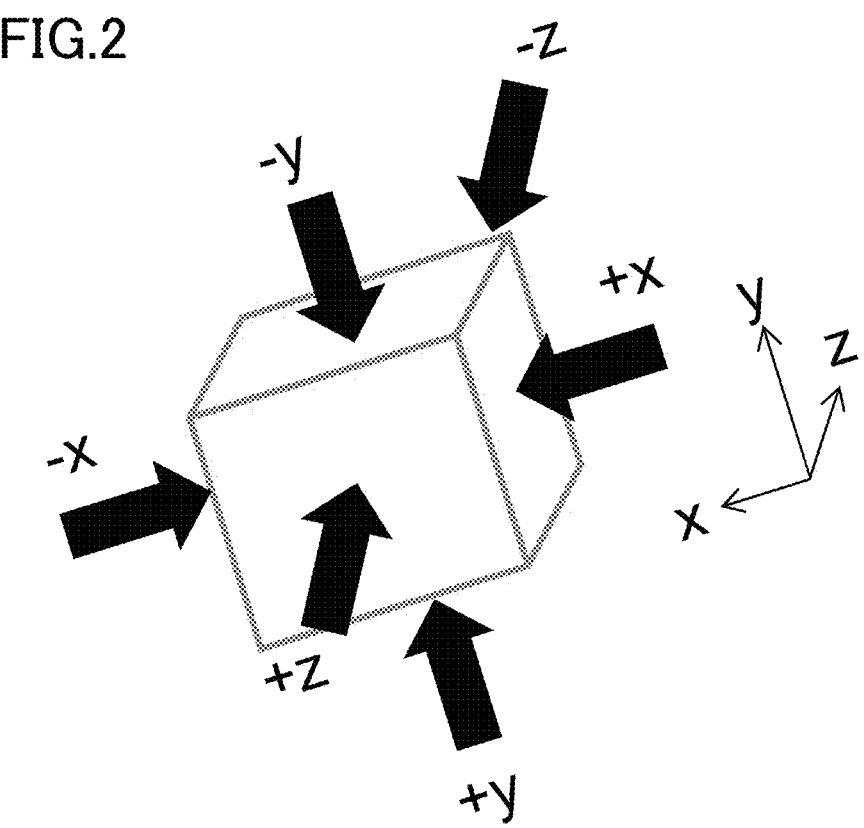
FIG. 2 shows a triaxial acceleration sensor that is used as one example of the tapping sensor unit described herein.

FIG. 1 shows the manipulator system 1 described herein, and FIG. 2 shows a triaxial acceleration sensor that is used as one example of the tapping sensor unit 22 described herein.

The manipulator system 1 according to one embodiment includes an operating unit 2 operated by an operator, a manipulator 3 operated by the operating unit 2, and a system control unit 4 that controls the manipulator 3 in association with the operation of the operating unit 2.

The operating unit 2 includes a master arm 21 operated by the operator, a tapping sensor unit 22 that detects vibrations or movements, and an impact sensor unit 23 that detects impacts or the like. The manipulator 3 includes a main manipulator unit 31 and a driver 32.

The master arm 21 conforms in shape to the main manipulator unit 31, and issues instructions about the operation of the main manipulator unit 31 and the driving of the driver 32. In association with movement of the master arm 21 by the operator, the system control unit 4 controls the driver 32 such that the main manipulator unit 31 moves in conformity with movement of the master arm 21.

The tapping sensor unit 22 includes a triaxial acceleration sensor that detects movements of three axes, an imaging sensor that images how they move to detect the presence or absence of vibrations, or the like. As can be seen from FIG. 2, the triaxial acceleration sensor that detects vibrations in the ±x, ±y and ±z directions.

The impact sensor unit 23 is located in a position corresponding to the operator's elbow to detect input with tapping by the operator's elbow. For instance, this sensor unit 23 may be a mono-axial acceleration sensor, a sensor that detects contacts, or the like.

Figure 3:
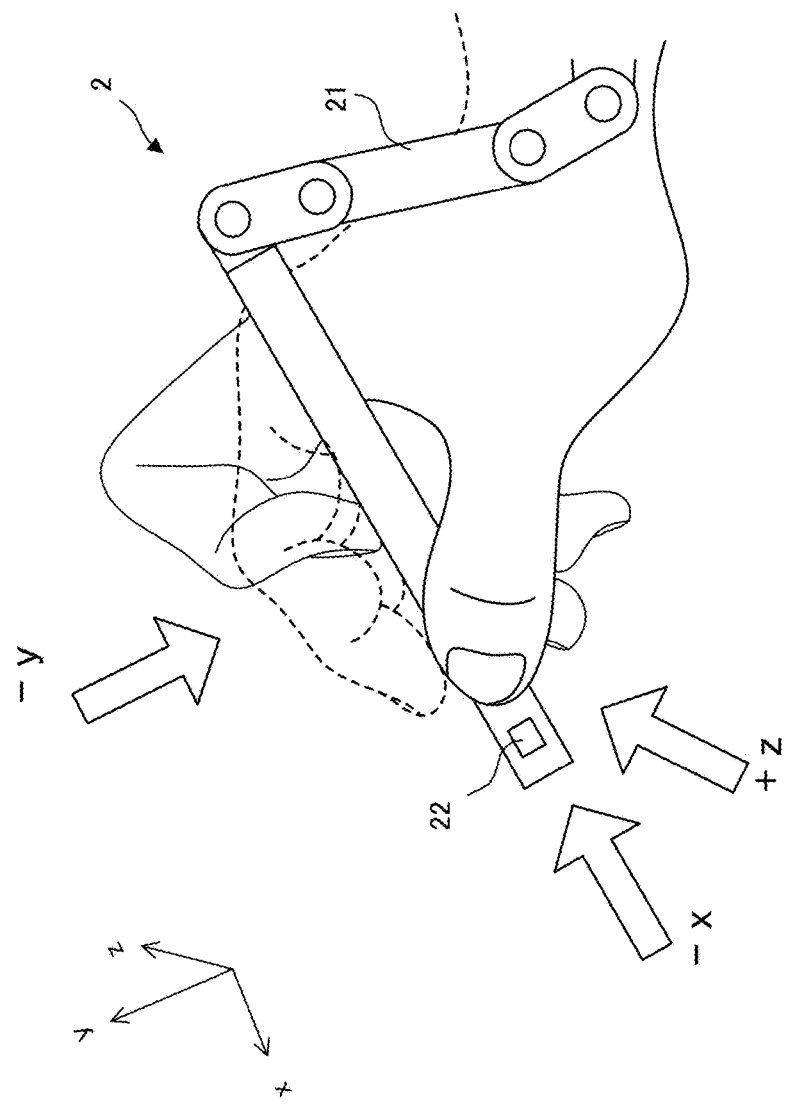
FIG. 3 is illustrative of one exemplary operation of the operating unit in the manipulator system described herein.
Figure 4:
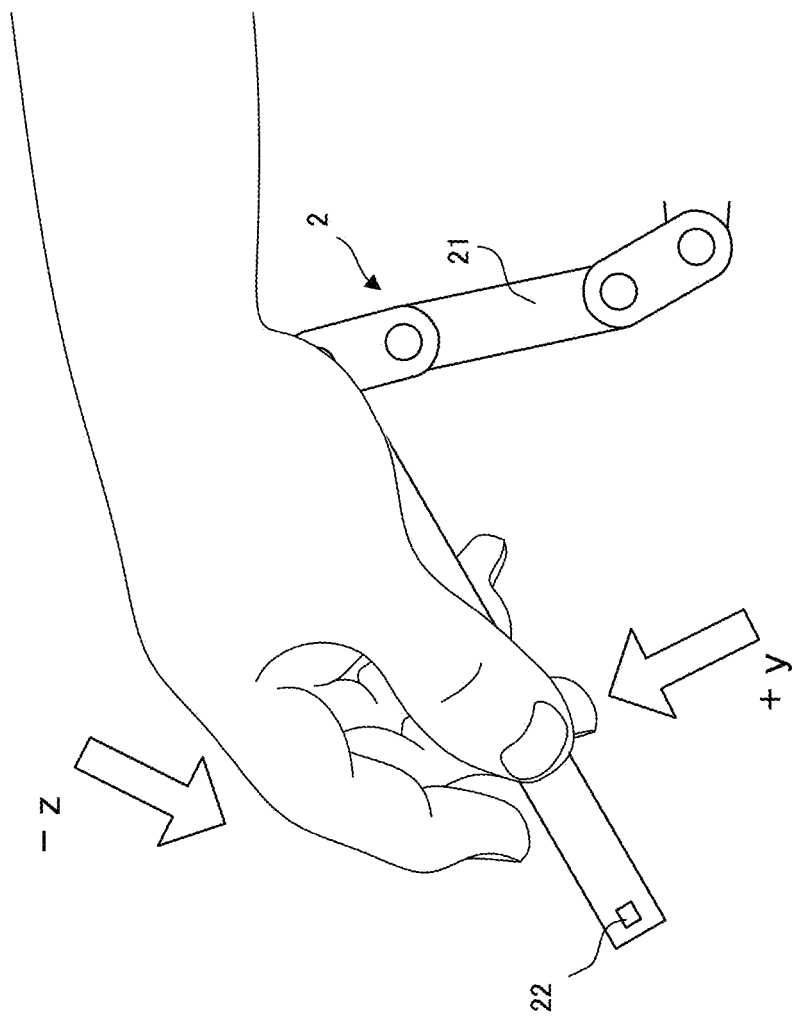
FIG. 4 is illustrative of another exemplary operation of the operation unit in the manipulator system described herein.

FIG. 3 shows one example of the operation of the operating unit 2 in the manipulator system 1 described herein, and FIG. 4 shows another example of the operation of the operating unit 2 in the manipulator system 1 described herein.

In operation, the operator grips the master arm 21 of the operating unit 2. As the operator puts the master arm 21 into movement, it allows for the main manipulator unit 31 to move in conformity with movement of the master arm 21.

Apart from this operation, and in the control unit 2 described herein, the operator taps the master arm 21 so that vibrations can be given on the tapping sensor unit 22, allowing for the main manipulator unit 31 to make settings changes, mode conversions, and so on.

When the operator taps the master arm 21 with the index finger or the like from above as shown in FIG. 3, the tap sensor unit 22 detects an input from the −y direct on, and when the operator taps the master arm 21 with the left hand, the index finger or the like from the front, the tap sensor unit 22 detects an input from the −x direction. Alternatively, when the operator taps the master arm 21 with the thumb or the like from the left side, the tap sensor unit 22 detects an input from the +z direction.

Likewise, when the operator taps the master arm 21 with the index finger or the like from the right side as shown in FIG. 4, the tap sensor unit 22 detects an input from the −z direction, and when the operator taps the master arm 21 with the middle finger or the like from below, the tap sensor unit 22 detects an input from the +y direction. Referring here to a direction such as the +x direction in which it is difficult for the operator to tap the master arm 21, such an impact sensor unit 23 as shown in FIG. 1 may be allocated to an input in the +x direction.

It is here to be understood that the setting changes, mode conversions or the like of the main manipulator unit 31 may be implemented depending on the intensity, number or interval of tappings, etc.

The medical system 10 that incorporates the manipulator system 1 described herein will now be explained.

Figure 5:
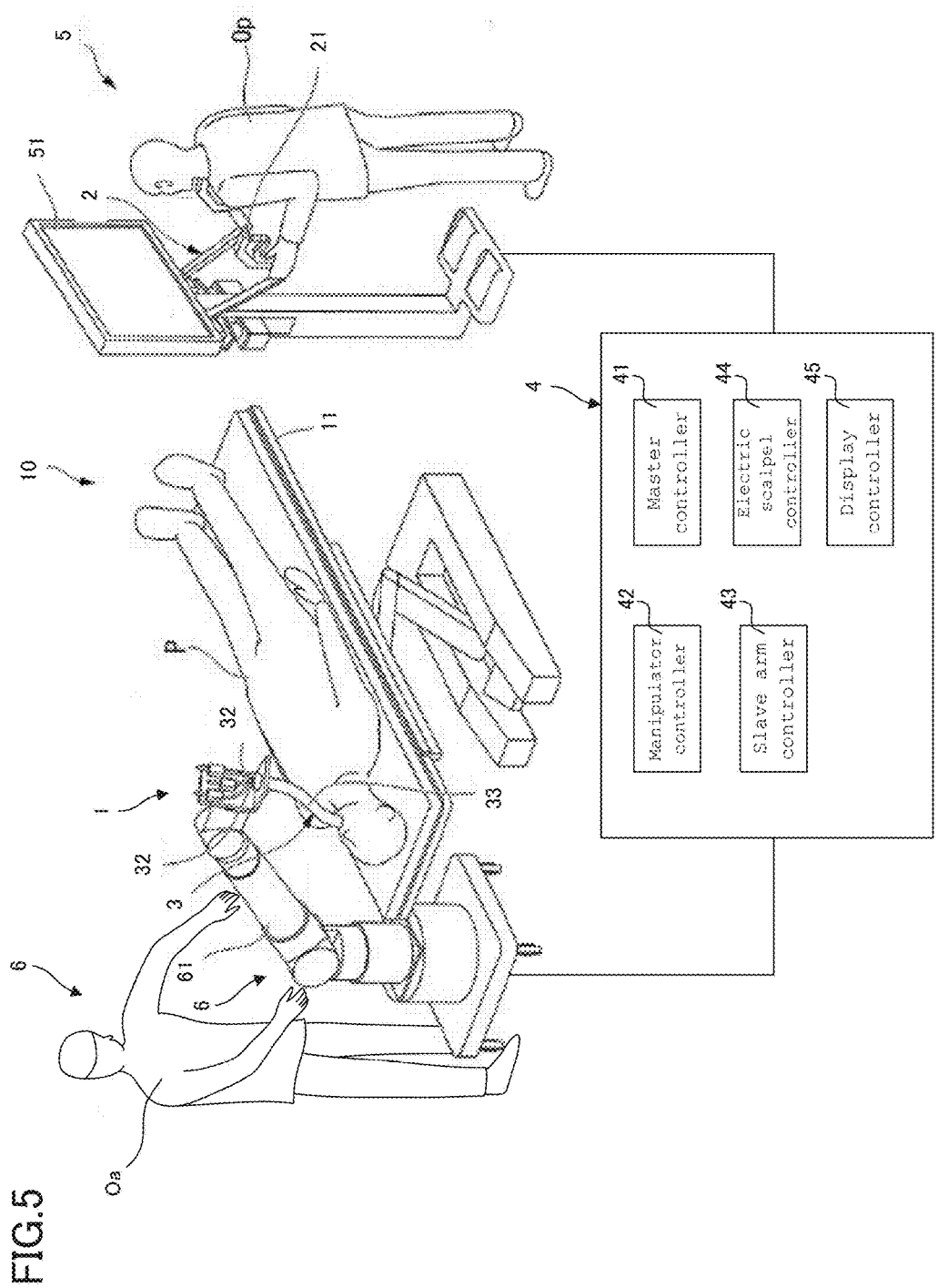
FIG. 5 shows the medical system 10 that incorporates the manipulator system 1 described herein.
Figure 6:
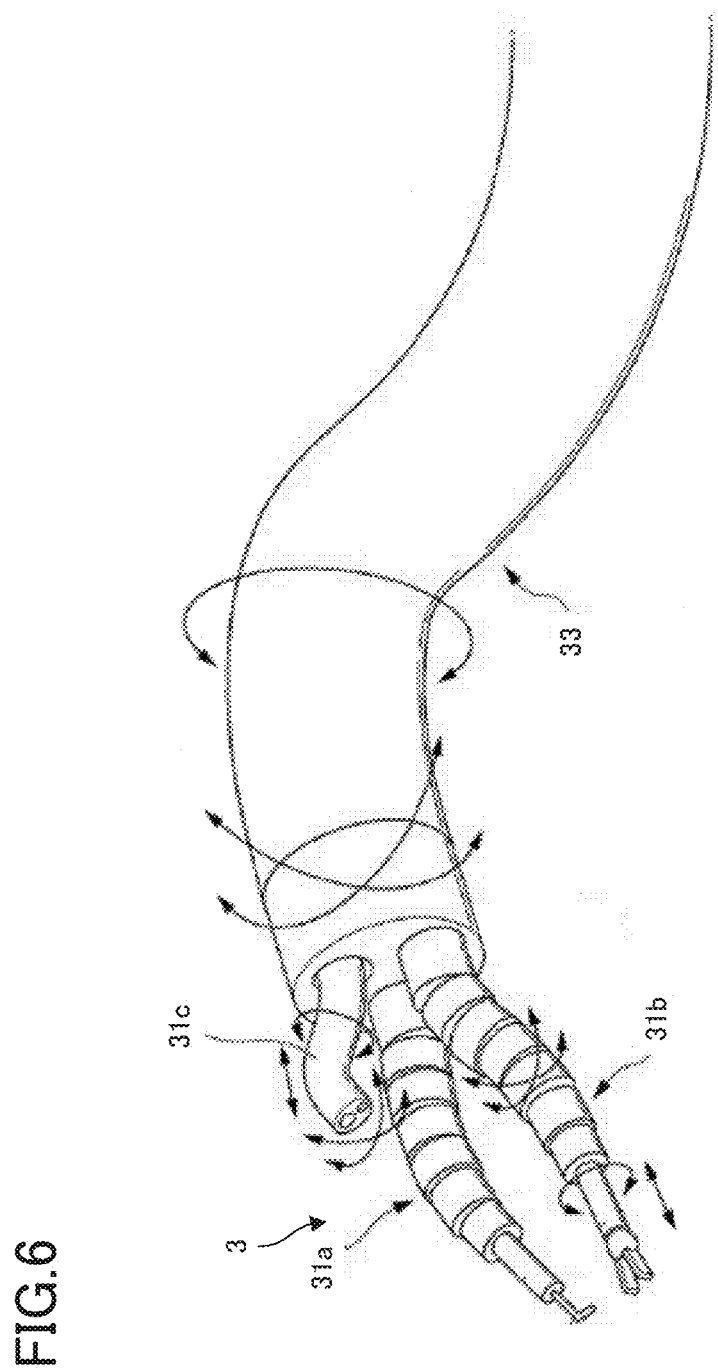
FIG. 6 shows one arrangement of the manipulator 3 at the distal end of the overtube 33 described herein.

FIG. 5 shows the medical system 10 that incorporates the manipulator system 1 described herein, and FIG. 6 is illustrative of the architecture of the manipulator 3 at the distal end of the overtube 33 described herein.

The medical system 10 described herein preferably operates in the master-slave mode. The medical system 10 includes an operating unit 2 including a master arm 21, a master input unit 5 for issuance of an operating command and a slave manipulator 6 including a slave arm 61, and implements remote control of the slave arm 61 and manipulator 3 in such a way as to keep track of the operation of the master arm 21 by an operator Op. An operating command is sent by way of the master arm 21 to a master controller 41 in the system control unit 4 where it is subjected to optional transformation processing, after which it is entered in a slave controller 43 or a manipulator controller 42. Thereafter, an operating signal sent from the manipulator controller 42 to the slave manipulator 6 to put the slave arm 61 and manipulator 3 into operation. An electric scalpel controller 44 gains control of output settings for an electric scalpel, etc., and a display controller 45 gains control of setting changes for an endoscope 31c and a display unit 51. These controllers may be accommodated up in a single casing or, alternatively, they may be built up by a combination of existing products.

As shown in FIG. 5, the slave manipulator 6 is placed on an operating table 11 on which a patient P lies down. The slave arm 61 includes a plurality of joints having a multi-degree of freedom so that it can be put into multi-axis operation. The respective joints having a multi-degree of freedom are individually driven by a power source (not shown) such as a servo motor having an incremental encoder or decelerator.

The slave arm 61 is provided at its distal end with the manipulator 3 that is inserted through the body cavity of the patient P for surgical procedures. As shown in FIG. 6, the manipulator 3 includes treatment tools 31a, 31b and an endoscope 31c, and is inserted through an overtube 33. The distal end of the overtube 33 is inserted through the body cavity of the patient P. A plurality of treatment tools 31a and 31b, because of being selectively used depending on the surgical procedure applied, are provided with different distal-end treatment structures or configurations; they may be attached to or detached from the distal end portion of the slave arm 61 for replacements or, alternatively, they may be inserted into or pulled out of a channel formed through the overtube 33 for replacements or diverse surgical procedures. The endoscope 31c acquires images of an operative field including the internal site of the patient's body to be operated by the treatment tools 31a and 31b.

The master input portion 5 includes a plurality of master arms 21 operated by an operator Op and a display unit 51 for displaying images acquired through the endoscope 31c. Each master arm 21 has a known construction capable of multi-axis movements, and is gripped by a surgeon to issue an operating command to a distal end side near to the operator Op.

The insert portion described herein includes a flexible, elongated overtube 33, and treatment tools 31a, 31b and endoscope 31c inserted through an insertion bore in the overtube 33 through which the manipulator is inserted. Note here that the treatment tools 31a, 31b and endoscope 31c have a structure applicable to the manipulator system 1 described herein.

The manipulator 3 described herein includes a first treatment tool 31a and a second treatment tool 31b. As an end effector, the first treatment tool 31a includes an electric scalpel and the second treatment tool 31b includes a hand grip. On the distal side the manipulator 3 is extendable from the overtube 33, and constructed of bending assembly in which there are plural joint rings arranged in an axial direction. Fixed to the most distal end side are both ends of an operating wire for driving the bending assembly, and the operating wire may be driven to bend the bending assembly. The bending assembly may also be rotated in the axial direction. Likewise, the overtube 33 per se may preferably be bent, and rotated in the axial direction as well.

According to the medical system 10 described herein, the slave arm 61, manipulator 3 and so on may be controlled by the master arm 21 of the operating unit 2. The master arm 21 described herein is provided with the tap sensor unit 22 shown in FIG. 1 such that the operator Op can tap the master arm 21 thereby making a switchover to the control mode for controlling the slave arm 61, manipulator 3, an electric scalpel that is the first treatment tool 31a or the display unit 51, or the like. With a tap in the +y direction, for instance, there is a switchover to the mode for controlling the slave arm 61, and with a tap in the −y direction, there is a switchover to the mode for controlling the manipulator 3, etc. Preferably, information corresponding to the mode applied is displayed on the display unit 51. Note here that the tap sensor unit 22 may be provided on the slave arm 61 or the like or, alternatively, it may be operated by another operator Op.

Figure 7:
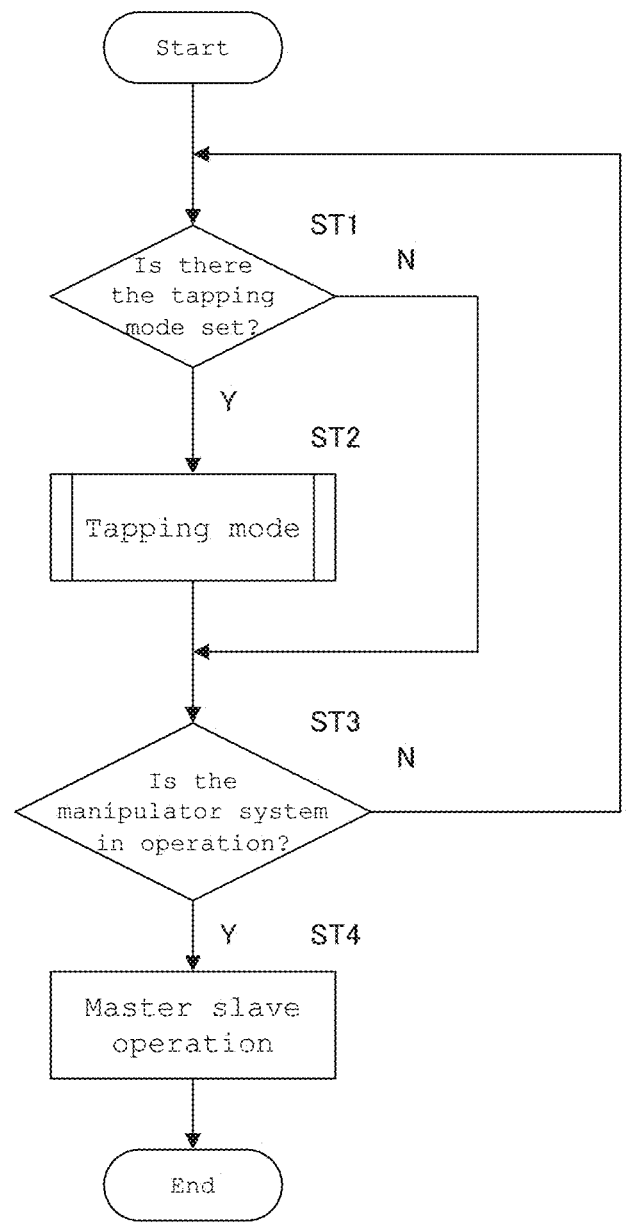
FIG. 7 is a control flowchart for the medical system described herein.

FIG. 7 is a tap control flowchart for the medical system described herein.

First of all, whether or not there is the tapping mode set is determined in Step 1 (ST1).

When there is the tapping mode in Step 1, the control process goes to Step 2 for the subroutine of the tapping mode (ST2) that will be described later. When there is no tapping mode in Step 1, the control process goes to Step 3.

Whether or not the manipulator system 1 is in operation is then determined in Step 3 (ST3). When the manipulator system 1 is not in operation in Step 3, the control process returns back to Step 1. When the manipulator system 1 is in operation, the control process goes to Step 4 for master-slave operation (ST4).

Figure 8:
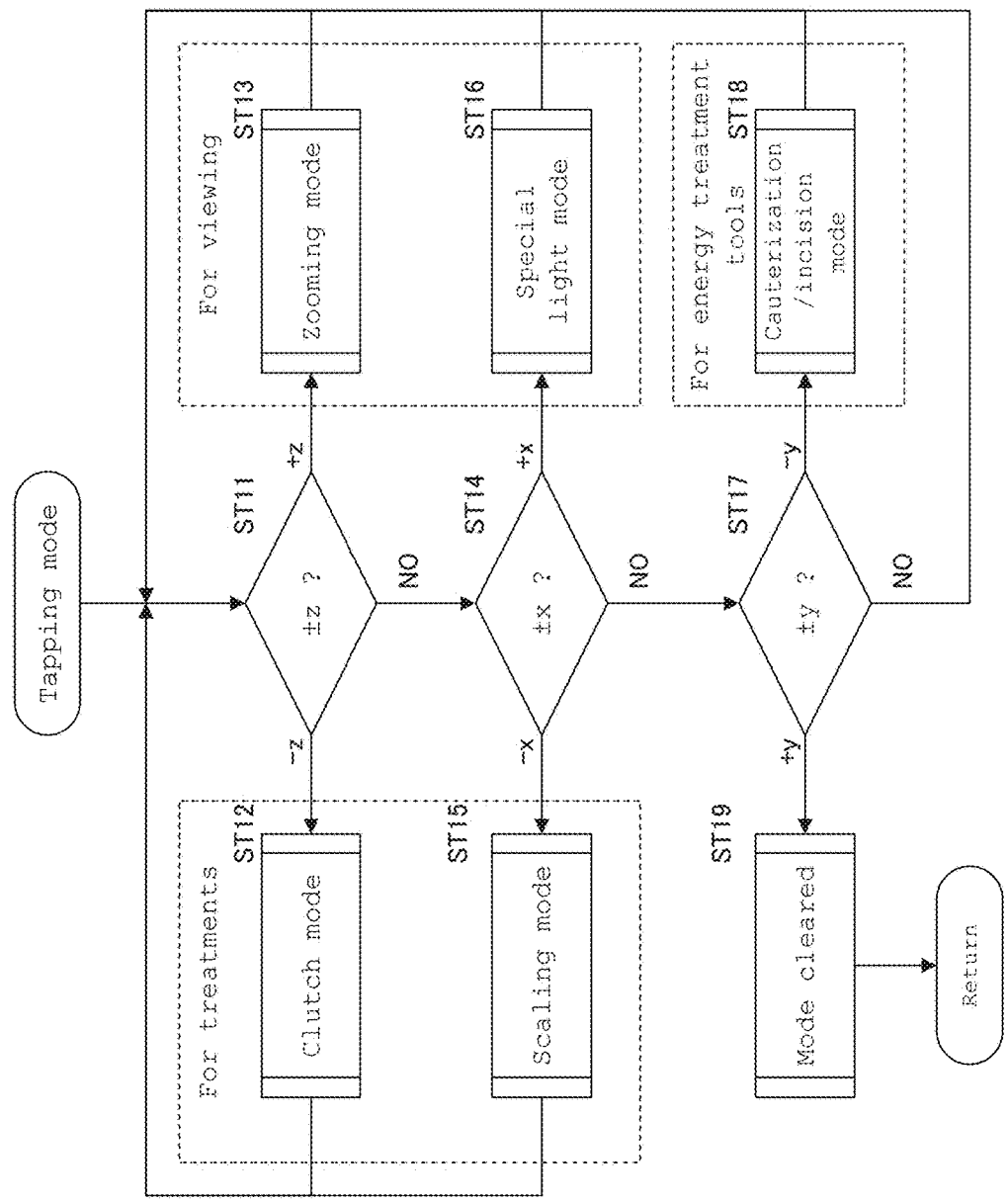
FIG. 8 is one exemplary control flowchart for the tapping mode of the medical system described herein.

FIG. 8 is one example of the control flowchart for the tapping mode of the medical system described herein.

As the control process goes to the subroutine of the tapping mode in Step 2 shown in FIG. 7, whether or not the tapping direction is in the ±z direction is first determined in Step 11 (ST11). When the tapping direction is the −z direction in Step 11, the control process goes to Step 12 in which there is a shift to a clutch mode for treatment tool connection/disconnection (ST12), after which the control process goes back to Step 11. When the tapping direction is the direction in Step 11, the control process goes to Step 13 is which there is a shift to a viewing zoom mode for endoscope zooming (ST13), after which the control process returns back to Step 11.

When the tapping direction is not the ±z direction in Step 11, whether or not the tapping direction is the ±x direction is determined in Step 14 (ST14). When the tapping direction is the −x direction in Step 14, the control process shifts to a treatment scaling mode for choosing a scaling function of varying the operating ratio between the master arm and the slave arm (ST15), after which the control process returns back to Step 11. When the tapping direction is the +x direction in Step 14, the control process goes to a viewing special light mode for choosing illumination light in Step 16 (ST16), after which the control process returns back to Step 11.

When the tapping direction is not the ±x direction in Step 14, the control process goes to Step 17 in which whether or not the tapping direction is the ±y direction is determined (ST17). When the tapping direction is the −y direction in Step 17, the control process goes to Step 18 in which there is a shift to a cauterization/incision mode of setting an output for an energy treatment, tool such an electric scalpel (ST18), after which the control process returns back to Step 11. When the tapping direction is the +y direction in Step 17, the control process goes to Step 19 in which the mode is cleared (ST19), and the control process then returns back to the control flow shown in FIG. 7. When the tapping direction is not the ±y direction in Step 17, the control process returns back to Step 11.

The modes of the medical system described with reference to FIG. 8 are by no means limited to those described and shown; other modes may be used as well.

According to the medical system described herein, it is thus possible to make ready shifts to the respective modes by tapping.

Controls in the modes will now be explained. Here take a clutch mode as an example of the embodiment.

Figure 9:
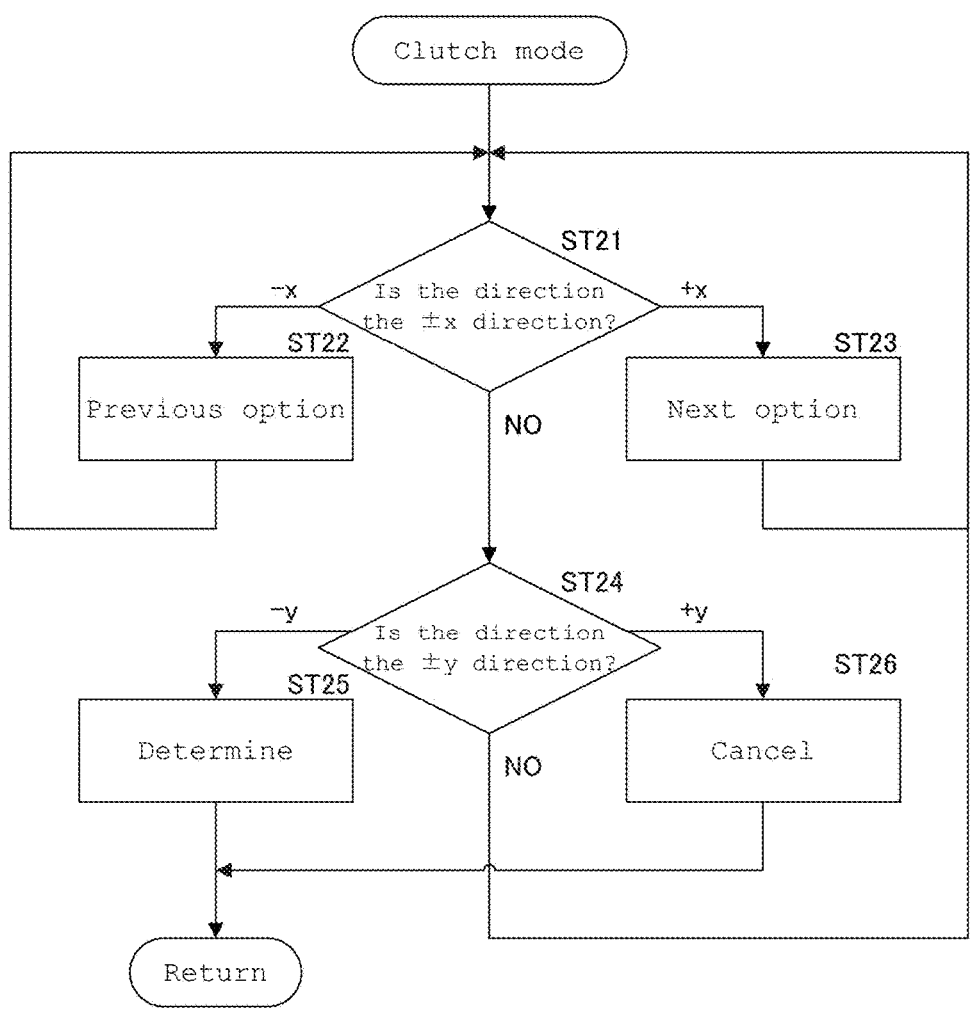
FIG. 9 is a control flowchart for the clutch mode.

FIG. 9 is one example of the control flowchart for the clutch mode.

In the clutch mode, whether or not the tapping direction is the ±x direction is first determined in Step 21 (ST21). When the tapping direction is the −x direction in Step 21, the control process goes to Step 22 in which the control process moves back to the previous option (ST22), after which it returns back to Step 21. When the tapping direction is the +x direction in Step 21, the control process goes to Step 23 in which it moves to the next option (ST23), after which the control process returns back to Step 21.

Figure 10:
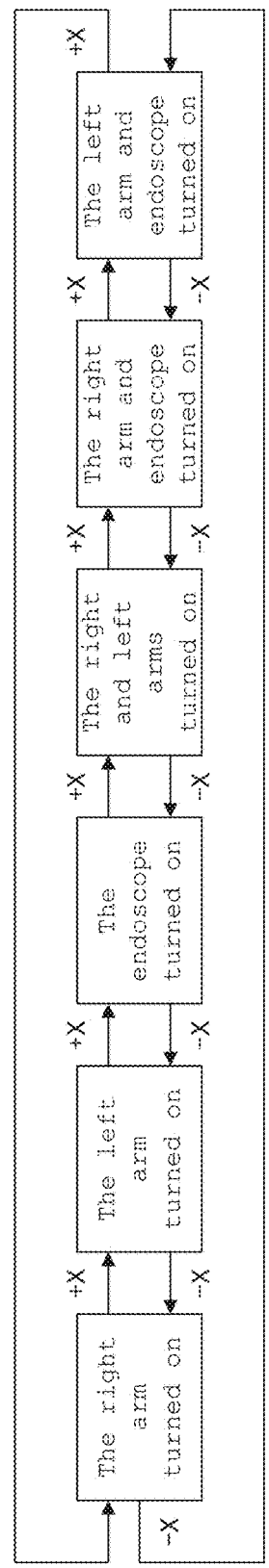
FIG. 10 is illustrative on one example of the clutch mode transition.

FIG. 10 shows one example of the clutch mode transition.

In the clutch mode, for instance, the master arm 21 is tapped in the ±x direction whereby connection/disconnection portions are sequentially selected. As shown typically in FIG. 10, the connection/disconnection of the treatment tools and endoscope may be selected for each tapping. When the endoscope is held on at the present movement in such a way as to be controllable, the treatment tools for the right arm and the left arm are turned on in such a way as to be controllable upon detection of a tap on the master arm 21 in the +x direction. Upon detection of a tap on the master arm 21 in the −x direction, the treatment tool for the left arm is selectively turned on in such a way as to be controllable.

When the tapping direction is not the ±x direction in Step 21, the control process goes to Step 24 to determine whether or not the tapping direction is the ±y direction (ST24). When the tapping direction is the −y direction in Step 24, the control process goes to Step 25 to determine an option to be selected (ST25), after which it returns back to Step 11 shown in FIG. 8. When the tapping direction is the −y direction in Step 24, the control process goes to Step 26 to cancel the selected option (ST26), after which it returns back to Step 11 shown in FIG. 8.

It is here to be noted that even in other modes, control may be implemented in such a flow as shown in FIG. 9. In this case, a different criterion for tapping may be relied upon. For instance, the criterion for tapping is defined by the tapping direction in the embodiment described herein; however, the criterion may be the number or intensity of tappings. Transitions within the modes of FIG. 10 may be set within the respective modes.

According to the medical system described herein, it is thus possible to facilitate selections in the respective modes by tapping by the operator.

According to the manipulator system 1, as described above, the operating unit 2 that is put by the operator into operation, the manipulator 3 that is operated by the operating unit 2, the system control unit 4 that controls the manipulator 3 in association with operation of the operating unit 2 and the tapping sensor unit 22, 23 for detecting tapping by the operator, it enables the system control unit 4 to switch between controls in association with information detected by the tapping sensor unit 22 so that diverse operations or manipulations are achievable in limited space.

According to the manipulator system 1 wherein, as described herein, the information detected by the tapping sensor unit 22 includes the direction, intensity or number of tappings and the system control unit 4 implements control set for each piece of information in association with the information detected by the tapping sensor unit 22, 23, it is possible to facilitate control by tapping by the operator, resulting in improvements in operability.

According to the manipulator system 1 wherein, as described above, the operating unit 2 includes the master arm 21 for coordination with the manipulator 3 and the tapping sensor unit 22 is provided on the master arm 21, it is possible to introduce much more improvements in operability.

According to the manipulator system 1 wherein, as described above, the system control unit 4 includes the clutch control for connection/disconnection of actuation of the manipulator 3 in association with information detected by the tapping sensor unit 22, it is possible to rapidly deactivate the manipulator 3 in case of emergency.

According to the manipulator system 10 incorporating the manipulator system 1 which, as described above, includes the master input unit 5 that includes the operating unit 2 for issuance of an operating command and the slave manipulator 6 including the slave arm 61 and manipulator 3 and in which the slave arm 61 is remotely controlled in such a way as to keep track of operation of the master arm 21, it is possible to achieve more diverse operations. It is also possible for another operator Oa to carry out tapping to determine a speed for positioning of the slave arm 61, facilitating location and positioning prior to surgical operations or changes in location incidental to position changing during surgical operations.

According to the medical system 10 wherein, as described herein, the manipulator 3 includes the treatment tools 31*a*, 31*b* and endoscope 31*c*, the master input unit 5 includes the display unit 51 adapted to display images taken through the endoscope 31*c* and the system control unit 4 makes a switchover between at least the treatment tool 31*a*, 31*h*, the endoscope 31*c* and the display unit 51 in association with information detected by the tapping sensor unit 22, 23, it is possible for the operator to facilitate selection by tapping.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Manipulator system
10: Medical system
2: Operating unit
21: Master arm
22: Tapping sensor unit
23: Impact sensor unit (tapping sensor unit)
3: Manipulator
31: Main manipulator unit
32: Driver
4: System control unit
5: Master input unit
6: Slave manipulator
61: Slave arm

The invention claimed is:

1. A manipulator system comprising:
a plurality of arms configured to be gripped by an operator and capable of being rotated with a joint as an axis such that a manipulator is put into actuation;
a tapping sensor that is provided on a distal end of a distal side arm of the plurality of arms, the tapping sensor detecting tapping by operation of the operator on the distal-side arm;
a system controller that implements control set for each tapping in association with the tapping detected by the tapping sensor.

2. The manipulator system according to claim 1,
wherein the tapping detected by the tapping sensor includes a direction of tapping, and
the system controller implements control for each direction of tapping in association with the direction of tapping detected by the tapping sensor.

3. The manipulator system according to claim 1,
wherein the tapping detected by the tapping sensor includes an intensity of tapping, and
the system controller implements control for each intensity of tapping in association with the direction of tapping detected by the tapping sensor.

4. The manipulator system according to claim 1,
wherein the tapping detected by the tapping sensor includes a number of tapping, and
the system controller implements control for each intensity of tapping in association with the number of tapping detected by the tapping sensor.

5. The manipulator system according to claim 1, wherein the system controller further includes clutch control for connection/disconnection of actuation of the manipulator in association with the tapping detected by the tapping sensor.

6. A medical system that incorporates the manipulator system according to claim 1,
wherein the manipulator further includes a slave arm mounted on a distal end thereof and a master arm comprising the plurality of arms so that the slave arm is remotely controlled in such a way as to keep track of operation of the master arm.

7. The medical system according to claim 6,
wherein:
the manipulator includes a treatment tool and an endoscope,
the medical system includes a display unit for displaying images taken by the endoscope, and
the system controller makes a switchover between controls of at least the treatment tool, the endoscope and the display in association with the tapping detected by the tapping sensor.

8. The manipulator system according to claim 1, further comprising an impact sensor that is separated from the plurality of arms to detect an impact inflicted by the operator on the arms, wherein the system controller uses the impact sensor to implement control set for each tapping in association with the impact on the arms.

* * * * *